(12) United States Patent
Brubaker et al.

(10) Patent No.: US 6,991,808 B2
(45) Date of Patent: Jan. 31, 2006

(54) PROCESS FOR THE PRODUCTION OF SUSTAINED RELEASE DRUG DELIVERY DEVICES

(75) Inventors: Michael J. Brubaker, Ft. Worth, TX (US); Pavlos Papadopoulos, Antioch, IL (US); Ramesh Krishnamoorthy, Apex, NC (US)

(73) Assignee: Bausch & Lomb Inc., Rochester, NY (US)

( * ) Notice: Subject to any disclaimer, the term of this patent is extended or adjusted under 35 U.S.C. 154(b) by 167 days.

(21) Appl. No.: 10/055,584

(22) Filed: Jan. 23, 2002

(65) Prior Publication Data

US 2002/0110635 A1    Aug. 15, 2002

Related U.S. Application Data

(60) Provisional application No. 60/264,441, filed on Jan. 26, 2001.

(51) Int. Cl.
*A61K 9/00* (2006.01)
*A61K 9/22* (2006.01)
*A61F 21/00* (2006.01)

(52) U.S. Cl. .................. 424/473; 424/423; 424/427
(58) Field of Classification Search ........... 604/290, 604/890.1; 427/2.1; 424/423–473; 514/772.2
See application file for complete search history.

(56) References Cited

U.S. PATENT DOCUMENTS

| 3,416,530 | A | | 12/1968 | Ness ........................ 128/260 |
|---|---|---|---|---|
| 3,618,604 | A | | 11/1971 | Ness ........................ 128/260 |
| 4,014,335 | A | | 3/1977 | Arnold ..................... 128/260 |
| 5,378,475 | A | * | 1/1995 | Smith et al. ............... 424/473 |
| 5,773,019 | A | | 6/1998 | Ashton et al. ............. 424/423 |
| 5,902,598 | A | * | 5/1999 | Chen et al. ................ 424/423 |
| 6,001,386 | A | * | 12/1999 | Ashton et al. ............. 424/423 |
| 6,413,540 | B1 | * | 7/2002 | Yaacobi ..................... 424/427 |
| 6,713,081 | B2 | * | 3/2004 | Robinson et al. ......... 424/427 |

OTHER PUBLICATIONS

Controlled Drug Delivery (Part I, Xue Shen Wu, PhD, pp. 32, 33, 44-46, 63, 66 & 67) Technomic Publishing Co., Inc., 1996.

* cited by examiner

*Primary Examiner*—Nicholas D. Lucchesi
*Assistant Examiner*—Roz Maiorino
(74) *Attorney, Agent, or Firm*—Paul Lavoie; Denis Polyn

(57) ABSTRACT

Disclosed is an improved sustained release drug delivery device and method of producing such device. The device comprises a drug core in an impermeable cup or impermeable coating layer that is adhered to an uncured suture tab and covered with a permeable polymer coating layer that is similar to the makeup of the suture tab. The permeable polymer coating layer that covers the device, covering the impermeable coating layer and at least a portion of the drug core, is cured (after drying) along with the uncured suture tab. The "cocuring" or one step curing process forms a very strong bond between the outer coating layer to the suture tab preventing leaks.

8 Claims, 1 Drawing Sheet

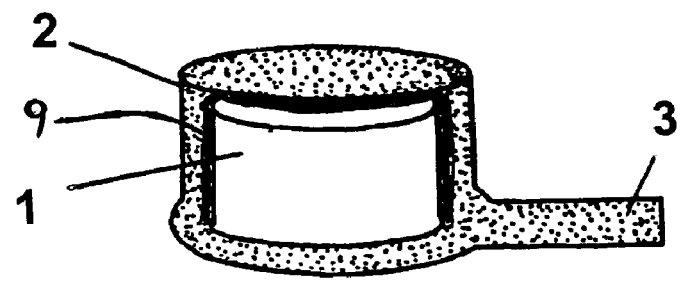
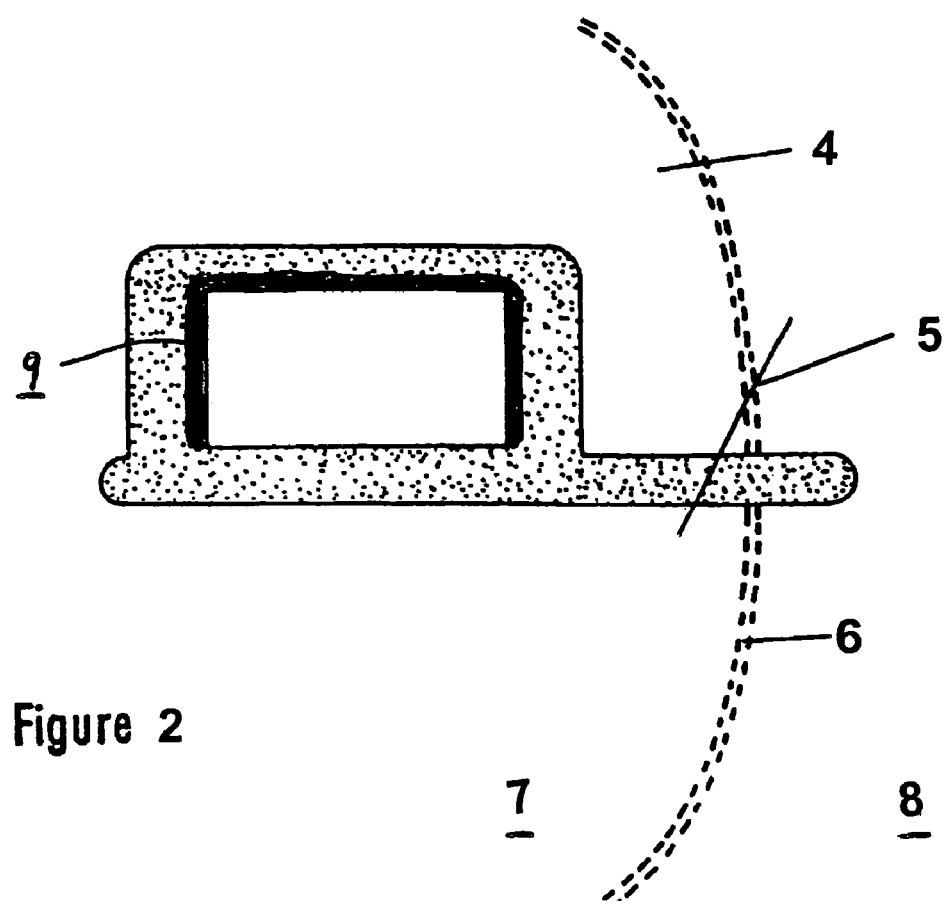

PROCESS FOR THE PRODUCTION OF SUSTAINED RELEASE DRUG DELIVERY DEVICES

This application claims the benefit of Provisional App. No. 60/264,441, filed Jan. 26, 2001.

FIELD OF THE INVENTION

The present invention relates to an improved process for producing a device for delivering drug directly to the interior portions of the body of a mammalian organism, such as to the eye. The drug delivery method includes administration of an agent effective in obtaining a desired diagnostic effect or local or systemic physiological or pharmacological effect by inserting in a desired location in the body of a mammalian organism a sustained release drug delivery device.

BACKGROUND

Over the years, various drugs have been developed to assist in the treatment of a wide variety of ailments and diseases. However, in many instances such drugs are not capable of being administered either orally or intravenously without the risk of various detrimental side effects.

CMV retinitis is a disease that is characterized by inflammation of the retina caused by infection with cytomegalovirus. CMV retinitis is one of the most common causes of sight-threatening infections among people with HIV. The symptoms include loss of visual acuity, blind spots, and the loss of peripheral vision. Left untreated, CMV retinitis can lead to blindness.

Intravenous ganciclovir (GCV) is effective in the treatment of CMV retinitis in AIDS patients, but bone marrow toxicity limits its usefulness. Continuous maintenance GCV therapy is necessary to prevent progression or recrudescence of the disease, but despite maintenance therapy a significant number of patients experience a relapse during treatment. Additionally, there are other risks and problems associated with systemic GCV administration.

Intravitreal GCV injections administered once or twice weekly have resulted in temporary remission of CMV retinitis in AIDS patients. Intravitreal GCV injections may provide a higher intraocular drug concentration than systemic therapy and reduce the incidence of neutropenia. However, current treatment of CMV retinitis in AIDS patients is clearly suboptimal. Ganciclovir is virustatic and thus disease inhibition requires maintenance drug administration.

A more detailed explanation of the use of intravenous GCV and intravitreal injections of GCV can be found in U.S. Pat. No. 5,902,598, herein incorporated in its entirety by reference. A discussion of the difficulties associated with the systemic therapy of cyclosporine A in the treatment of uveitis can be found in U.S. Pat. Nos. 5,773,019 and 6,001,386, herein incorporated in their entirety by reference.

Accordingly, there exists a strong need for the elimination of the undesirable physiological problems associated with GCV treatment of CMV retinitis, while maintaining the advantageous properties of this treatment. Although delivering the drug locally with injections may minimize the systemic toxicity of GCV, repeated injection is not a practical mode of administration.

Due to the risks that certain drugs impose, researchers have developed systems for administering such drugs to aid in the treatment of these ailments and diseases. A general discussion of drug delivery control systems is provided in Controlled Drug Delivery (Part I), Xue Shen Wu, Ph.D. pp32, 33, 44–46, 63, 66, and 67 (Technomic Publishing Co. Inc., 1996), the entire contents of which are incorporated herein by reference. The systems have been designed largely to reduce and to control the release rate of incorporated drugs. However, these systems failed to achieve many of the advantages solved by later devices.

For example, U.S. Pat. No. 4,014,335 to Arnold, relates to various ocular inserts that act as a deposit or drug reservoir for slowly releasing a drug into the tear film for prolonged periods of time. These inserts are fabricated as a three-layer laminate of flexible polymeric materials that are biologically inert, non-allergenic, and insoluble in tear fluid. To initiate the therapeutic programs of these devices, the ocular inserts are placed in the cul-de-sac between the sclera of the eyeball and the eyelid for administering the drug to the eye. Multiple layer laminate systems can present a challenge to reproducibly manufacture and are more difficult to produce by large-scale or commercial manufacturing procedures.

The device of U.S. Pat. No. 3,416,530 is manufactured with a plurality of capillary openings that communicate between the exterior of the device and the interior chamber generally defined from a polymeric membrane. While the capillary openings in this construction are effective for releasing certain drugs to the eye, they add considerable complexity to the manufacture of the device because it is difficult to control the size of these openings in commercial manufacturing using various polymers.

U.S. Pat. No. 3,618,604 describes a device that does not involve such capillary openings, but instead provides for the release of the drug by diffusion through a polymeric membrane. The device, as disclosed in a preferred embodiment, comprises a sealed container with the drug contained in an interior chamber. Nonetheless, as described in U.S. Pat. No. 4,014,335, certain problems have been identified with such devices such as the difficult task of sealing the margins of the membrane to form the container. In addition, stresses and strains introduced into the membrane walls from deformation during manufacturing of those devices may cause the reservoir to rupture and leak.

U.S. Pat. No. 6,001,386 to Ashton, et al. relates to an implantable sustained release drug delivery device with an inner core containing an effective amount of a low solubility agent covered by a non-bioerodible polymer coating layer that is permeable to the low solubility agent disclosed.

The above described systems and devices are intended to provide sustained release of drugs effective in treating patients at a desired local or systemic level for obtaining certain physiological or pharmacological effects. However, there are many disadvantages associated with their use, including the fact that it is often difficult to obtain the desired release rate of the drug (either too much or too little drug is released into the body). Further, it is difficult to adhere the device to the tab that is used to suture the device inside of the organ, such as an eye. Great effort is expended to ensure a strong bond of the device to this "suture tab." Even if the device is strongly adhered to the suture tab, it is a difficult task to completely seal all of the margins and prevent rupture and leaking of drug into the body.

The need for a better release system is especially significant in the treatment of CMV retinitis. Thus, there remains a long-felt need in the art for an improved device for providing sustained release of a drug to a patient to obtain a desired local or systemic physiological or pharmacological effect.

Prior to the development of the present invention, there was a drug delivery device developed that ameliorated many of the problems associated with sustained release drug delivery. The device, which is disclosed in U.S. Pat. No. 5,378,475 (incorporated herein by reference in its entirety), included a first coating essentially impermeable to the passage of the effective agent and a second coating permeable to the passage of the effective agent. In the device, the first coating covered at least a portion of the inner core; however, at least a small portion of the inner core is not coated with the first coating layer. The second coating layer essentially completely covers the first coating layer and the uncoated portion of the inner core. The portion of the inner core which is not coated with the first coating layer allows passage of the agent into the second coating layer thus allowing controlled release.

While the devices described in U.S. Pat. No. 5,378,475 solve many of the aforementioned problems pertaining to drug delivery, the devices and the method of making the devices are not without some problems. In particular, polymers suitable for the second coating of the inner core are frequently relatively soft and technical difficulties can arise in production of uniform films that do not rupture and leak. This is especially true when attempting to coat non-spherical bodies with edges (such as a cylindrical shape or edges of a suture tab). In such cases, relatively thick films must be applied to achieve uninterrupted and uniform coatings, which adds significant bulk to the device. Thus, the devices tend to be larger than necessary as a result of the thickness needed to seal the ends of the inner core and seal it to the suture tab. In addition to adding bulk, multiple layer devices are more difficult to manufacture reproducibly and are more difficult to produce by commercial manufacturing procedures. Also, the various layers can be made of materials that are relatively incompatible with one another adding to the difficulties in coating. Often devices such as these require a plurality of manual assembly steps that is time consuming, limits available supply, and adds variability.

U.S. Pat. No. 5,902,598 also presents solutions to some of the problems associated with manufacturing small devices. The device in U.S. Pat. No. 5,902,598 includes a third permeable coating layer that essentially completely covers the device. While the third coating layer improves the structural integrity of the device and helps to prevent potential leakage, some manufacturing difficulties can limit scaled up manufacturing. For example, consistent application of the outermost coating layer and reproducibility in manufacturing can be problems with designs which require manual assembly, a significant number of steps in the assembly process, or outer dip coatings.

The problem of device size is extremely important in the design of devices for implantation into the limited anatomical spaces such as small organs like the eye. Larger devices require more complex surgery to both implant and remove. The increased complexity can result in complication, longer healing or recovery periods, and potential side effects (e.g. increased chance of astigmatism). Further, the extra polymer required to achieve a uniform coating reduces the potential internal volume of the implant and hence limits the amount of drug that can be delivered, potentially limiting both efficacy and duration.

Also, failure of some of these devices in use can lead to a dumping of the agent, which can cause harm to the mammalian organism being treated.

It would, therefore, be desirable to have a structurally stable device that can be reproducibly manufactured and manufactured by commercial techniques. As a result of all of the above, there remains a long felt need in the art for an improved device and an improved process of producing such a device for providing sustained release of a drug to a mammalian organism to obtain a desired local or systemic physiological or pharmacological effect, especially for ocular use.

SUMMARY OF THE INVENTION

The sustained release drug delivery device according to the present invention comprises:
  a) a drug core comprising at least one agent effective in obtaining a diagnostic effect or effective in obtaining a desired local or systemic physiological or pharmacological effect;
  b) an impermeable coating layer impermeable to the passage of said agent that surrounds a portion of said drug core;
  c) a suture tab adhered to and extending from said drug delivery device that is used during surgery to adhere said device to the body of a mammalian organism; and
  d) a permeable polymer coating layer, permeable to the passage of said agent that essentially completely covers the impermeable coating layer b) and the uncoated portion of the drug core a) that is not coated with said impermeable coating layer:

wherein the polymer coating layer d) is of a similar polymer material as said suture tab c) and both polymer coating layer and suture tab have been cured at the same time, bonding both together.

This invention is also directed to a method for providing controlled and sustained administration of an agent effective in obtaining a desired local or systemic physiological or pharmacological effect comprising inserting in a desired location in the body of a mammalian organism the sustained release drug delivery device above.

The method of manufacturing a sustained release drug delivery device according to the present invention comprises:
  A) providing a drug core comprising at least one agent effective in obtaining a diagnostic effect or effective in obtaining a desired local or systemic physiological or pharmacological effect;
  B) coating a portion of said drug core with an impermeable coating layer impermeable to the passage of said agent;
  C) coating the resulting coated core of B ) with an outer coating of a permeable polymer coating layer, permeable to the passage of said agent that essentially completely covers the impermeable coating layer of B) and the uncoated portion of the drug core of A) that is not coated with said impermeable coating layer; and
  D) curing the resulting device of C) at a temperature of about 130° C. to about 160° C. for about 1 to about 5 hours:

wherein an uncured solid polymer suture tab has been adhered to the device prior to step D) such that a portion of said suture tab extends away from said device and the curing of step D) jointly cures the uncured solid polymer suture tab and the permeable polymer coating layer of C) and wherein the permeable polymer coating layer applied in C) is of a similar polymer material as said solid polymer suture tab.

BRIEF DESCRIPTION OF THE DRAWINGS

FIG. 1 is a schematic perspective view of a sustained drug delivery device according to various embodiments of this invention.

FIG. 2 is a schematic view illustrating the device of FIG. 1 attached to the eye.

DETAILED DESCRIPTION OF THE INVENTION

The drawings, which are not drawn to scale, are set forth to generally illustrate the sustained release drug delivery device of the present invention.

FIGS. 1 and 2 show an embodiment of the present invention with a coated drug core 1 that is coated with coating. This coating is preferally composed of an inner impermeable coating layer 9 adjacent the drug core 1 and an outer permeable polymer coating layer 2 on the exterior of the device. The device includes a suture tab 3. The permeable polymer coating layer 2 and suture tab preferally appear as an integral single unit made of the same material.

According to this aspect of the present invention, once the device has been constructed with the uncured outer coating layer attached to the uncured suture tab, it is cured. This forms a strong destructible bond between the suture tab and permeable polymer.

FIG. 2 also illustrates how the suture tab 3 is used to attach the device to a structure of the mammalian body, inside an organ such as the eye 4 with suture 5, where eye wall 6 separates inside eye 7 and outside eye 8.

The inventors have unexpectedly discovered a sustained release drug delivery device design and manufacture method that provides a structurally stable, safe device that can be more easily and reproducibly manufactured than current designs that are known in the art. The inventors have unexpectedly discovered that the suture tab can be assembled with the device uncured and then cured when the outer permeable coating layer is cured. This unexpectedly provides a device that has a much stronger "destructive" bond between the suture tab and the outer polymer coating.

In one preferred embodiment, the device includes an impermeable cup made of silicone with an attached polyvinyl alcohol (PVA) suture tab, the cup acts as a reservoir for a drug core containing an agent such as fluocinolone acetonide. A hole through the proximal end of the suture tab enables a suture to be used for securing the device. The open end of the cup permits drug to diffuse out of the core, through the PVA suture tab, and out of the outer permeable polymer coating layer. An inner core is formed of a pellet of fluocinolone acetonide. The device is formed by coating the cup holding the pellet and the attached suture tab with a permeable polymer solution of 10% PVA. The PVA coating is allowed to dry. The device is then cured at 135–145° C. The dry uncured suture tab is cured as the outer coating layer is also cured.

According to the process of the present invention, the curing time and temperature can vary, depending upon the extent of curing desired. Generally this curing is done at a particular temperature (such as between about 130° C. and about 160° C.) for a time until a color change from clear to amber is seen. The darker the amber the more the polymer like PVA is cured. The cure time can be fairly long or short depending upon the cure temperature and the desired extent of curing and is preferably between about 1 and about 5 hours.

The suture tab and the outer permeable polymer coating layer need to be made of compatible materials such that, upon curing a strong bond is formed between the two. The strength of the bond is a result of the curing of like polymer coatings, which upon heating or curing form a continuous crystalline lattice framework. This bond is generally so strong that it is a destructive bond.

By "destructive" bond, it is meant such a bond that when the suture tab is attempted to be pulled away and separated from the rest of the device, the bond is so strong that either the device or the suture tab is destroyed at separation.

Alternatively, another aspect of the present invention entails a sustained release drug delivery device comprising:

1) a coated drug core comprising an inner core comprising at least one agent effective in obtaining a diagnostic effect or effective in obtaining a desired local or systemic physiological or pharmacological effect and a permeable polymer coating layer, the polymer being permeable to the passage of said agent, wherein the permeable polymer coating layer covers at least a portion of the inner core;

2) an impermeable coating layer impermeable to the passage of said agent that surrounds only a portion of said coated drug core; and 3) a suture tab adhered to and extending from said drug delivery device that is used during surgery to adhere said device to the body of a mammalian organism:

wherein the permeable polymer coating layer covering at least a portion of the inner core in is of a similar polymer material as said suture tab and both polymer coating layer and suture tab have been cured at the same time and wherein said inner core is completely covered by a combination of permeable polymer coating layer, impermeable coating layer, and suture tab such that the agent is able to diffuse out of the inner core through the permeable polymer coating layer or permeable suture tab.

The sustained drug delivery device according to the above alternate aspect of the present invention alternatively can have said impermeable coating layer of essentially covering the entire drug core of. In this aspect at least one passageway must then be made through said impermeable layer allowing passage of said agent out of said inner core, through said polymer coating layer, and out of said passageway.

The expression "agent" as used herein broadly includes any compound, composition of matter, or mixture thereof that can be delivered from the device to produce a beneficial and useful result.

The term "impermeable" refers to a material that is sufficiently impermeable to environmental fluids as well as ingredients contained within the delivery device, such that the migration of such fluids and ingredients into or out of the device through the impermeable material is so low as to have substantially no adverse impact on the function of the device.

The term "permeable" refers to a material that is capable of being passed through or permeated. Permeating includes passing through openings, holes, pores, or intersections.

The term "drug core" refers to any drug supply, drug depot, drug in suspension, reservoir or drug matrix. It includes one or more agents necessary to obtain the desired diagnostic effect or local or systemic physiological or pharmacological effect. It includes any excipients, suspending agents, or binders. Reference may be made to any standard pharmaceutical textbook such as Remington's Pharmaceutical Sciences. The drug core can be in liquid form, solid form, in dispersion, or any other form known in the art. Solid dose includes all conventional solid dose forms known in the art including the preferred tablets and pellets. Dispersions include all conventional forms known in the art, such as liquid in liquid dispersions and solid in liquid dispersions.

The expression "passageway" as used herein comprises means and methods suitable for releasing the agent from the device. The expression includes an aperture, orifice, or bore through the device. The passageway can be formed by mechanical procedures such as erosion, laser, or molding; and chemical procedures.

The device according to the present invention functions by delivering active drug agent out of the device into a structure of the mammalian body. The agent diffuses out of the drug core, out the open end of the impermeable coating layer or cup, and through the permeable polymer coating layer. Glue, polymers, or other adhesion means can be employed to further bond the drug core to the cup. However, by curing both the suture tab and the outer permeable polymer coating layer together, the bond is generally sufficient without the use of an adhesive.

The device has an attached suture tab with a hole through the proximal end through which a suture can be placed to anchor the device to a structure of the organism requiring treatment. Providing a suture hole at the proximal end of the suture tab of the device enables the surgeon to attach the device without additional steps. The proximal end of the suture tab is at the point of attachment, i.e. the point where the suture is used to attach the device to the body. The preferred point of attachment is at the end of the suture tab opposite the cup/reservoir/drug core.

The location of the suture and the structure the device is sutured to can be any that meet with current surgical techniques known in the art, such as the sclera of the eye.

By curing both the suture tab and the outer permeable polymer coating layer together, the bond is generally sufficient without the use of an adhesive and provides structural integrity to the device, and facilitates manufacturing and handling as a solid structure. In addition, by eliminating the suture tab curing step, prior to it being attached onto the cup, the process and design decreases the number of steps and reduces the chance for variability in the size and shape of the device.

The invention further relates to a method for treating a mammalian organism to obtain a desired local or systemic physiological or pharmacological effect. The method includes administering the sustained release drug delivery device to the mammalian organism and allowing the agent effective in obtaining the desired local or systemic physiological or pharmacological effect to pass out of the inner core, out the open end of the impermeable coating or cup, and through the permeable polymer layer. The term "administering", as used herein, means positioning, inserting, implanting, or any other means for exposing the device to a mammalian organism. The route of administration depends on a variety of factors including type of response or treatment, type of agent, and the preferred site of administration. However, the preferred method is to insert the device into the target organ and suture it into place. In ocular applications, more preferably through a surgical procedure into the vitreous of the eye followed by suturing the device in place.

In combination with the examples above, a variety of methods may also be utilized to provide adhesion of the drug core to the cup portion of the device. These methods include the use of adhesives, polymers such as PVA, or any other procedure known in the art to provide adhesion at the points of contact between the drug core, the cup, and/or the suture tab. The methods of co-curing to improve adhesion will vary depending on the materials that the components are manufactured from, so long as the suture tab and the outer permeable polymer coating layer are compatible.

For example, the drug cores or the cups of the present invention can also be treated before or after assembly with an adhesive, which would serve to further secure the drug core in the device. The sealant must be permeable to the agent or agents in the device. For example, a few drops of a permeable polymer could be placed in the unitary cup before inserting the drug core into the cup device and prior to attaching the suture tab to the open end of the cup. Alternative points of attachment of the suture tab is also permitted.

The drug core contains an agent effective in obtaining a desired local or systemic physiological or pharmacological effect. The following classes of agents could be incorporated into the devices of the present invention: anesthetics and pain killing agents such as lidocaine and related compounds and benzodiazepam and related compounds; anti-cancer agents such as 5-fluorouracil, adriamycin and related compounds; anti-fungal agents such as fluconazole and related compounds; anti-viral agents such as trisodium phosphomonoformate, trifluorothymidine, acyclovir, ganciclovir, DDI and AZT; cell transnort/mobility impending agents such as colchicine, vincristine, cytochalasin B and related compounds; antiglaucoma drugs such as beta-blockers: timolol, betaxolol, atenalol, etc; antihypertensives; decongestants such as phenylephrine, naphazoline, and tetrahydrazoline; immunological response modifiers such as muramyl dipeptide and related compounds; peptides and proteins such as cyclosporin, insulin, growth hormones, insulin related growth factor, heat shock proteins and related compounds; steroidal compounds such as dexamethasone, prednisolone and related compounds; low solubility steroids such as fluocinolone acetonide and related compounds; carbonic anhydrize inhibitors; diagnostic agents; antiapoptosis agents; gene therapy agents; sequestering agents; reductants such as glutathione; antipermeability agents; antisense compounds; antiproliferative agents; antibody conjugates; antidepressants; bloodflow enhancers; antiasthmatic drugs, antiparasiticagents; non-steroidal anti inflammatory agents such as ibuprofen; nutrients and vitamins; enzyme inhibitors; antioxidants; anticataract drugs; aldose reductase inhibitors; cytoprotectants; cytokines, cytokine inhibitors, and cytokin protectants; uv blockers; mast cell stabilizers; and anti neovascular agents such as antiangiogenic agents like matrix metalloprotease inhibitors.

Examples of such agents also include neuroprotectants such as nimodipine and related compounds; antibiotics such as tetracycline, chlortetracycline, bacitracin, neomycin, polymyxin, gramicidin, oxytetracycline, chloramphenicol, gentamycin, and erythromycin; antiinfectives; antibacterials such as sulfonamides, sulfacetamide, sulfamethizole, sulfisoxazole; nitrofurazone, and sodium propionate; antiallergenics such as antazoline, methapyriline, chlorpheniramine, pyrilamine and prophenpyridamine; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone and triminolone; miotics and anti-cholinesterase such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; and prodrugs such as those described in Design of Prodrugs, edited by Hans Bundgaard, Elsevier Scientific Publishing Co., Amsterdam, 1985. In addition to the above agents, other agents suitable for treating, managing, or diagnosing conditions in a mammalian organism may be placed in the drug core and administered using the sustained release drug delivery devices of the current invention. Once again, reference may be made to any standard pharmaceutical textbook such as Remington's Pharmaceutical Sciences for the identity of other agents.

Any pharmaceutically acceptable form of such a compound can be employed in the practice of the present invention, i.e., the free base or a pharmaceutically acceptable salt or ester thereof. Pharmaceutically acceptable salts, for instance, include sulfate, lactate, acetate, stearate, hydrochloride, tartrate, maleate and the like.

A large number of polymers can be used to construct the devices of the present invention. The only requirements are that they are inert, non-immunogenic and of the desired permeability. Materials that may be suitable for fabricating the device include naturally occurring or synthetic materials that are biologically compatible with body fluids and body tissues, and essentially insoluble in the body fluids with which the material will come in contact. The use of rapidly dissolving materials or materials highly soluble in body fluids are to be avoided since dissolution of the wall would affect the constancy of the drug release, as well as the capability of the device to remain in place for a prolonged period of time.

Naturally occurring or synthetic materials that are biologically compatible with body fluids and eye tissues and essentially insoluble in body fluids which the material will come in contact include, but are not limited to, glass, metal, ceramics, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasiticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4'-isopropylidene diphenylene carbonate), vinylidene chloride, acrylonitrile copolymer, vinyl chloride-diethyl fumerale copolymer, butadiene/styrene copolymers, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer and vinylidene chloride-acrylonitride copolymer.

In the preferred embodiment of the present invention the drug core is a solid tablet; the impermeable coating layer is made of a prefabricated silicone cup; the suture tab is a prefabricated tab of dried uncured PVA; and the outer permeably polymer coating layer is PVA, coated in liquid form over the cup and a portion of the suture tab. This assembly is then allowed to set while the PVA outer coating dries. The entire device is then cured at about 130° C. to about 150° C. for about 1 to about 5 hours.

The device can be formulated in any convenient shape. For example, the device can be 5 of any geometric shape dimensionally suitable for insertion in the eye. Thus, the device can be ellipsoid, rectangular, round, etc.

The dimensions of the device can vary with the size of the device, the size of the core or reservoir, and the membrane that surrounds the core or reservoir. The physical size of the device should be selected so that it does not interfere with physiological functions at the implantation site of the mammalian organism. The targeted disease state, type of mammalian organism, location of administration, and agents or agent administered are among the factors which would effect the desired size of the sustained release drug delivery device.

The devices according to the present invention may be made in a variety of ways . For example, if the cup or reservoir is going to be made entirely of polymer, then the polymer can be injection molded or die cast into a desired shape and size. The drug core can be made as any solid dose form such as a tablet or pellet. The drug core can also be coated with permeable polymer using any coating means currently known in the art. The drug core could also be formed with an inner core that is a drug in liquid form or suspension that is encapsulated in a permeable polymer.

The reservoir can be made in one piece, such as by encapsulating the drug core then boring out the desired passageway(s) and then coating with the outer permeable polymer coating layer. The size or number of passageways can be selected to achieve the desired release rate. The reservoir can also be formed using a unitary cup and inserting a plug of impermeable material. The assembled device having at least one passageway to permit the active drug to diffuse out through the outer permeable polymer coating layer. The unitary cup can have lip(s) or groove(s) around the open top end which interact with the impermeable plug holding it in place and closing the open top end of the cup. Due to the elastic nature of some polymers, such as silicone, the same result could also be achieved by essentially molding the reservoir as one piece and stretching the passageway wide enough to insert the drug core through the passageway.

The preceding descriptions of how to make the devices of the present invention is merely illustrative and should not be considered as limiting the scope of the invention in any way. In particular, the methods of making the device depend on the identity of the agent.

The devices can be surgically implanted at or near the site of action. This is the case for devices of the present invention used in treatment of ocular conditions, primary tumors, rheumatic and arthritic conditions, and chronic pain. The devices can also be implanted subcutaneously, intramusclarly, intraarterially, or intraperitoneally. This is the case when devices are to give sustained systematic levels and avoid premature metabolism.

Once in place, the device functions as a drug reservoir gradually releasing drug to the organ such as the eye and surrounding tissue. This device is particularly useful for treating ocular conditions such as glaucoma, proliferative vitreoretimopathy, diabetic retinopathy, uveitis, and keratitis. The device is also particularly useful as an ocular device in treating mammalian organisms suffering from cytomegalovirus retinitis wherein the device is surgically implanted within the vitreous of the eye.

As would be readily understood by one skilled in the art, the preferred amounts, materials, and dimensions depend on the method of administration, the effective agent used, the polymers used, the desired release rate and the like. Likewise, actual release rates and release duration depend on a variety of factors in addition to the above, such as the disease state being treated, the age and condition of the patient, the route of administration, as well as other factors which would be readily apparent to those skilled in the art. All of the forgoing U.S. Patents and other publications are expressly incorporated by reference herein in each of their entities.

Thus, the devices of the present invention provide many important advantages over previously known sustained release drug delivery devices. The co-curing of the suture tab and the outer permeable polymer coating layer design of the present invention provide an improved device that maintains its physical and chemical integrity in both the environments of use and in the presence of agent during the controlled and continuous dispensing of agent over a prolonged period of time.

Due to the structural integrity of the present design, the need for multiple outer layers can be minimized, i.e. a plurality of dip coating steps are not generally needed to prevent device failure and "dumping" of the agent. The ease of making the devices of the present invention minimizes stresses, strains, and deformations during manufacture, which may cause the reservoir to rupture and leak. The leaking of agent can result in harm to the patient and is a significant concern in the manufacture of implantable devices.

The co-cured device design of the present invention results in a device that is more easily and reproducibly manufactured then current designs known in the art and minimizes the number of steps and decreases potential variability in assembly. The present design also allows for mechanized manufacture. Eliminating all or part of manual assembly greatly decreases the potential variability in the finished product. In addition, the co-curing design and method eliminates the difficulties of sealing the margins faced by other devices in the prior art. This permits the therapeutic program to be precisely controlled and the release of drug to be constant and predicted with accuracy.

Another advantage of the devices of the present invention is the ease of construction by more standard manufacturing techniques into devices with different release rates. The number and size of the passageways in the reservoir embodiment of the present invention can be used to control diffusion properties to achieve a desired release rate. Varying the composition of the drug core can also be used to achieve a desired release rate. The same reservoir can be used for implants with different release rates making it possible to use a single manufacturing line or type of equipment.

The following specific examples demonstrate the sustained release drug delivery device design of the present invention. However, it is to be understood that these examples are for illustrative purposes only and do not purport to be wholly definitive as to the conditions and scope.

EXAMPLE 1

A device according to the present invention is prepared. The cup is made of silicone. The suture tab is dried uncured PVA. A drug core is formed as a pellet composed of 2.5 mg of fluocinolone acetonide. The drug core pellet is then inserted into the cup. The suture tab is glued to the drug core/cup assembly with a 10% solution of PVA. The assembly is coated with a 10% solution of PVA. The PVA coated assembly is dried and then cured for 5 hours at 135–145° C. A hole is then made at the end of the tab opposite the end that is glued to the cup.

EXAMPLE 2

The device of example 1 above is placed in a vial with 2.0 mL of a release media of 0.1 Sodium Acetate, pH 4.2. The vial is maintained in a 37° C. bath for 24 hours. After 24 hours, the vial is inverted to ensure homogeneity and the device is removed to a new vial with fresh media. This process is repeated for each day. The media is tested to determine the amount of the drug and verifies that it is being released from the device. From the data that is collected, the release rate of the device can be determined.

From the foregoing description, one of ordinary skill in the art can easily ascertain the essential characteristics of the instant invention, and without departing from the spirit and scope thereof, can make various changes and/or modifications of the inventions to adapt it to various usages and conditions. As such, these changes and/or modifications are properly, equitably, and intended to be, within the full range of equivalence of the following claims.

The invention claimed is:

1. A sustained release drug delivery device comprising:
   a) a drug core comprising at least one agent effective in obtaining a diagnostic effect or effective in obtaining a desired local or systemic physiological or pharmacological effect;
   b) an impermeable coating layer impermeable to the passage of said agent adjacent to said drug core that surrounds a portion of said drug core;
   c) a suture tab adhered to and extending from said drug delivery device that is used during surgery to adhere said device to the body of a mammalian organism; and
   d) a permeable polymer coating layer that is made of a similar polymer material as said suture tab, permeable to the passage of said agent that essentially completely covers the impermeable coating layer and the uncoated portion of the drug core that is not coated with said impermeable coating layer, wherein the sustained release delivery device is made by the step of curing both the polymer coating layer and the suture tab at the same time to bond both together.

2. The sustained release drug delivery device according to claim 1, wherein said suture tab is solid but made of an uncured polymer prior to the step of curing.

3. The sustained release drug delivery device according to claim 1, wherein said impermeable coating layer b) is a cup and said drug core a) is a solid that is shaped to be inserted into said cup.

4. The sustained release drug delivery device according to claim 1, wherein said inner core comprises a plurality of agents.

5. The sustained release drug delivery device according to claim 1, wherein said inner core comprises an effective amount of a low solubility agent.

6. The sustained release drug delivery device according to claim 1, wherein said agent is selected from a group consisting of immune response modifiers, neuroprotectants, corticosteroids, angiostatic steriods, anti-parasitic agents, anti-glaucoma agents, anti-biotics, anti-sense compounds, anti-angiogentic compounds, differentiation modulators, anti-viral agents, anti-cancer agents, and nonsteroidal anti-inflammatory agents.

7. The sustained release drug delivery device according to claim 1, wherein said impermeable coating layer is made of a polymer or a metal.

8. The sustained release drug delivery device according to claim 1, wherein said suture tab has a hole through the proximal end through which a suture can be placed to anchor the device to a structure of a mammalian body.

* * * * *